United States Patent [19]

Robuchon-Merovak et al.

[11] 4,104,031
[45] Aug. 1, 1978

[54] APPARATUS FOR DISPLAYING THE RESULTS OBTAINED ON AN AGGLUTINATION SUPPORT

[75] Inventors: Romain Gabriel Robuchon-Merovak, Levallois-Perret; Christian Romain Robuchon-Merovak, Paris, both of France

[73] Assignee: Readymatie S.A., Lausanne, Switzerland

[21] Appl. No.: 638,462

[22] Filed: Dec. 8, 1975

[51] Int. Cl.² .................................................. G01N 33/16
[52] U.S. Cl. .................................... 23/253 R; 354/75; 354/105; 356/39; 424/11
[58] Field of Search .................. 23/230 B, 253 R; 424/11; 356/39

[56] References Cited
U.S. PATENT DOCUMENTS

| | | | |
|---|---|---|---|
| 3,432,268 | 3/1969 | Unger | 23/230 B |
| 3,453,941 | 7/1969 | Marachy | 354/75 X |
| 3,502,437 | 3/1970 | Mass | 424/11 X |
| 3,533,744 | 10/1970 | Unger | 23/230 B |
| 3,617,222 | 11/1971 | Matle | 424/11 X |
| 3,635,680 | 1/1972 | Peoples | 424/11 X |
| 3,873,273 | 3/1975 | Moran | 23/253 R |
| 3,905,772 | 9/1975 | Hartnett | 23/230 B X |

Primary Examiner—Sidney Marantz
Attorney, Agent, or Firm—Roylance, Abrams, Berdo & Farley

[57] ABSTRACT

Apparatus for projecting, in conventional indication form, i.e. A, B, AB or O followed by the sign + or −, the results which enable an individual's blood group and rhesus factor to be determined and which are obtained with mixtures of blood taken from the individual and of different, appropriate, test sera. The apparatus comprises four positive luminous sighting members, representing a state of agglutination of the mixtures, four negative luminous sighting members, representing a state of non-agglutination of the mixtures, four electric switches controlled by levers which are each actuated towards one or other of these sighting members, from a middle position, depending on the results obtained with the mixtures, and five further luminous sighting members causing the letters A, B and O and the signs + and − to appear in dependence on the direction in which the levers are actuated to display the definition of the blood group. The apparatus is intended for use with a blood typing installation.

9 Claims, 9 Drawing Figures

APPARATUS FOR DISPLAYING THE RESULTS OBTAINED ON AN AGGLUTINATION SUPPORT

The invention is concerned with the typing of an individual's blood.

To type an individual's blood one mixes samples of his blood with various test-sera, here anti-A, anti-B, anti-AB and anti-D, one deposits the different mixtures on a so-called agglutination plate, one examines the plate to see whether or not there has been any agglutination in the mixtures, one determines, on the basis of the results obtained, the blood group of the tested blood, and one prepares a corresponding record card.

These operations can give rise to handling errors, errors in the interpretation of the results and/or errors of transcription. Now, such errors, as is known, can have grave consequences since they can be the cause of an individual's death in the even of a blood transfusion. It is therefore important to avoid them.

Thus, it has been proposed to design an installation which enables, firstly, the mixing and depositing operations to be carried out automatically, and, secondly, in order to avoid having the results of one individual being attributed to another, the individual's portrait and the agglutination plate to be recorded simultaneously with a camera after obtaining the results.

Since only a specialist would be capable of interpreting the results of the test, it has moreover been proposed to dispose adjacent the agglutination plate an auxiliary plate bearing the information that is needed to enable a person without any special knowledge to identify the blood group of the individual whose blood has been tested, to wit the conventional indication A, B, AB or O followed by the sign + or −, as the case may be, such auxiliary plate being photographed at the same time as the agglutination plate. It has also been proposed to include in the photograph the name of the individual and other possible information.

By providing this auxiliary blood-group-defining plate new possibilities for error are introduced since a laboratory assistant or other person will first have to interpret the results obtained on the agglutination plate and then select an auxiliary plate before placing the latter adjacent the agglutination plate.

The invention provides apparatus intended, in particular, for use with an installatin of the kind indicated and which is capable of reducing these new error possibilities.

The apparatus according to the invention serves to display, in conventional indication form, to wit A, B, AB or O followed by the sign + or −, the results which enable an individual's blood group and rhesus factor to be determined and which are obtained with mixtures of blood taken from the individual and of different, appropriate, test sera, and is characterized in that it comprises at least one positive visual indicator element, representing a state of agglutination of said mixtures, at least one negative visual indicator element, representing a state of non-agglutination of said mixtures, which is spaced from said first element, a plurality of electrical switches corresponding in number to that of said mixtures and controlled by levers which are disposed between said visual indicator elements and which are each actuated towards one or other of said elements, from a middle position, depending on the results obtained with said mixtures, and sighting members causing the letters A, B and O and the signs + and − to appear in dependence on the direction in which the levers are actuated to display the definition of said blood group.

In a particular form of embodiment of the apparatus, the sighting members are luminuous sighting members, electrically connected to the switches, that respectively bear the letters A, B and O and the signs + and − and which light up in dependence on the direction in which the levers are actuated. This form of embodiment of the apparatus helps to facilitate the interpretation of the results on an agglutination support.

Another form of embodiment of the apparatus, intended for use with a blood typing installation having a screen onto which are projected the results obtained on a so-called agglutination support, enables the auxiliary plate and hence the error potential that exists in the choice of the latter to be eliminated. In this embodiment the sighting members comprise windows formed in said screen, the letters A, B and O and the signs + and − being borne by movable supports behind the windows.

Figure 1:
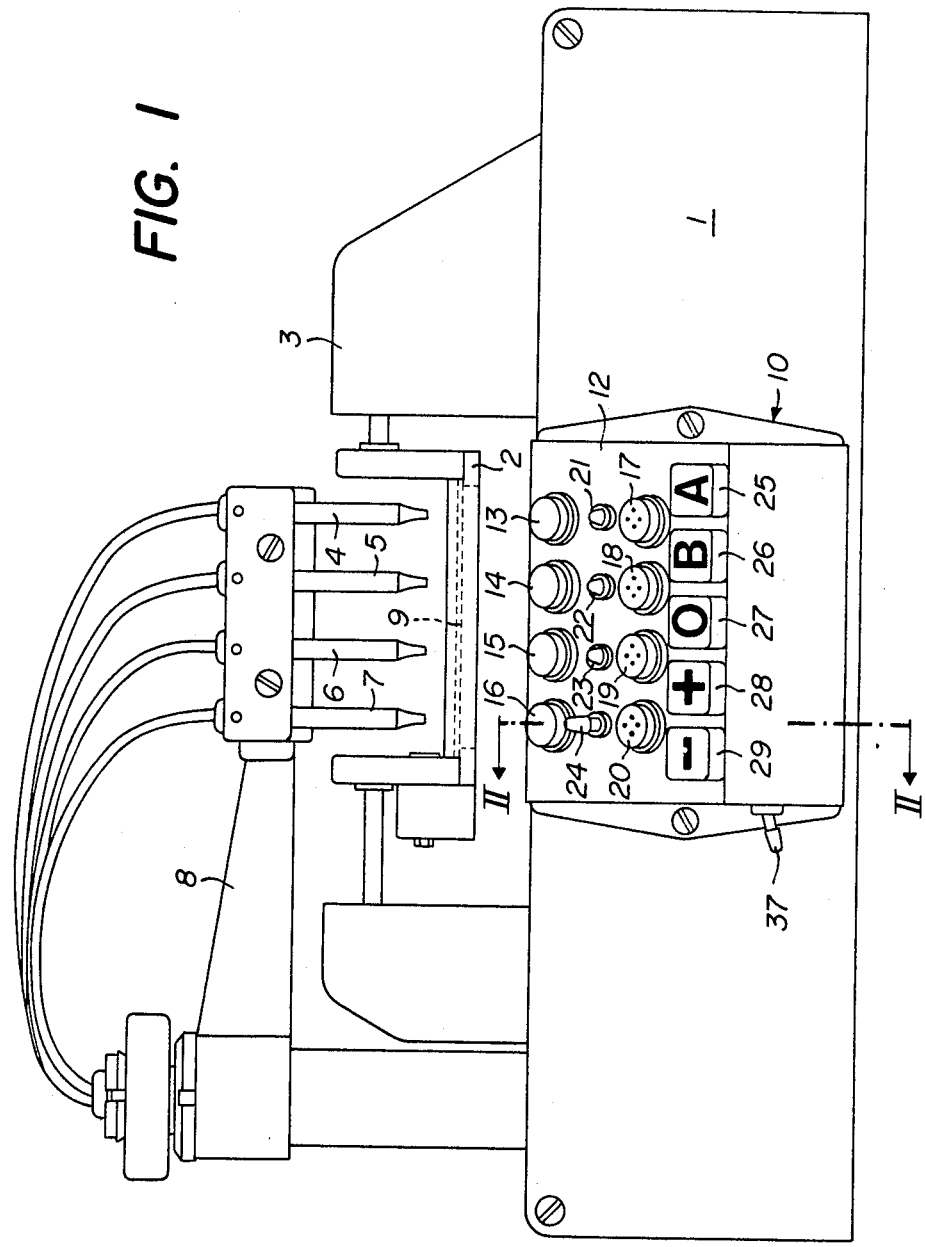
FIG. 1 illustrates a form of embodiment of the apparatus according to the invention that is secured to the rear wall of a blood typing installation of the kind set forth.

The blood typing installation on the rear wall 1 of which is secured the first form of embodiment of the apparatus according to the invention, comprises a cradle 2 carried by an agitating device 3. Above the cradle 2 are four pipettes 4, 5, 6 and 7 carried by a rotatable arm 8 and respectively containing a mixture consisting, firstly, of blood taken from the individual whose blood group and rhesus factor are to be determined and, secondly, of anti-A serum, anti-B serum, anti-AB serum and anti-D serum. In the cradle 2 is placed an agglutination plate 9 made of glass on which are deposited four drops of mixture by the four pipettes 4 to 7.

The apparatus comprises a casing 10 secured by screws to the wall 1. The casing has a front, panel forming, wall 12 in which are arranged a horizontal series of four luminous sighting members 13, 14, 15 and 16 each having an illuminable uniformly red face, a horizontal series of four luminous sighting members 17, 18, 19 and 20 each having an illuminable red-dotted white face, a horizontal series of four levers 21, 22, 23 and 24 disposed between the two series of sighting members 13 to 16 and 17 to 20, and a horizontal series of five luminous, definition, sighting members 25, 26, 27, 28 and 29 respectively bearing in black the letters A, B and O and the signs + and −.

Each of the levers 21 to 24 is disposed in alignment with a pair of sighting members respectively belonging to the series 13 to 17 and 17 to 20. Thus, lever 21 is in alignment with sighting members 13 and 17, lever 22 is in alignment with sighting members 14 and 18, etc. The levers can be actuated from a middle position either downwards, the position occupied by levers 21 to 23, or upwards, the position occupied by lever 24.

The levers 21 to 24 respectively control switches 30, 31, 32 and 33 inside the casing 10. The switches 30 to 33 are connected by a central terminal $a$ to an electric current supply line 34. They moreover each comprise a lower terminal $b$ and an upper terminal $c$. The sighting members 13-16 each comprise a terminal $d$ and a terminal $e$, FIG. 3, and the sighting members 17 to 20 each comprise a terminal $f$ and a terminal $g$, and the sighting members 25 to 29 each comprises a terminal $h$ and a terminal $i$. The terminals $b$ are each connected to one of the terminals $d$, the terminals $c$ are each connected to one of the terminals $f$, the terminals $e$ and $g$ are each connected to a supply line 35, and the terminals $i$ are each connected to a central terminal $j$ of a switch 36, controlled by a lever 37, which is secured to one of the side walls of the casing 10 and which further comprises a terminal $k$ connected to the supply line 35. The terminals $c$ of switches 30, 31 and 32 are also connected to the terminals $h$ of sighting members 25, 26 and 28, respectively, and the terminals $b$ of switches 32 and 33 are also connected to the terminals $h$ of sighting members 27 and 29 respectively.

As will be apparent from FIG. 1, the spacing of sighting members 13 to 16 and 17 to 20, and hence of levers 21 to 24, is chosen so as to correspond to that of the pipettes 4 to 7, and the casing 10 is secured to the wall 11 so that each pair of sighting members, such as 16 to 20, is aligned with one of the pipettes 4 to 7.

Thus, the row of members 13, 21 and 17 is aligned with pipette 4 and hence with the drop of blood and anti-A serum mixture that it will have deposited on the plate 9, and so on with the other three rows of members.

When the pipettes 4 to 7 will have each deposited a drop of the mixture they contain on the plate 9 and when the agitating device will duly have agitated the plate 9, the laboratory assistant or other operator required to note the results of the reactions in the drops on the plate, first examines the drop deposited by pipette 4. If the reaction has been positive, i.e. if agglutination has taken place, he actuates lever 21 from its middle position towards the sighting member 17 (whose red-dotted white face is reminiscent of the speckled appearance which a drop tends to take when there has been a reaction) which lights up. If, however, the reaction has been negative, i.e. if no agglutination has taken place, the operator actuates the lever 21 towards the sighting member 13 (whose uniformly red face is reminiscent of the uniform aspect of a drop of mixture in which no reaction has taken place). The operator actuates levers 22 to 24 in the same manner in accordance with the results he has observed on the plate 9. When all four levers have been actuated, he actuates lever 37 downwards and two or three of the sighting members 25 to 29 light up to display one of the following definitions: A+, A−, B+, B−, AB+, AB−, O+ and O−. The lever 37 can if desired be actuated at the start so that the definition of a blood group can take place progressively as the levers 21 to 24 are being actuated.

Figure 3:
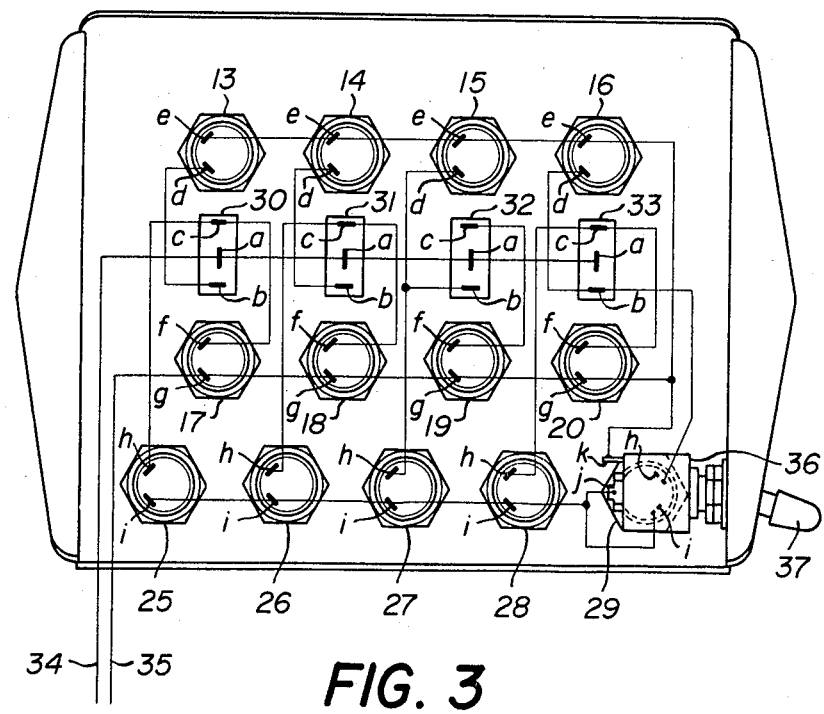
FIG. 3 is a rear view of the apparatus shown in FIGS. 1 and 2, illustrating the electrical wiring.

As is apparent from the wiring shown in FIG. 3, the lighting up of sighting members 13 to 16 (the negative sighting members) and of the sighting members 17 to 20 (the positive sighting members) produces the following results on the definition sighting members 25 to 29 (insofar as the switch 36 is on):

the switching on of the anti-A negative sighting member (13) has no effect on the definition sighting members 25 to 29;

the switching on of the anti-A positive sighting member (17) lights up the A defining sighting member (25);

the switching on of the anti-B negative sighting member (14) has no effect on the definition sighting members 25 to 29;

the switches on of the anti-B positive sighting member (18) lights up the B defining sighting member (26);

the switching on of the anti-AB negative sighting member (15) lights up the O defining sighting member (27);

the switching on of the anti-AB positive sighting member (19) has no effect, on the definition sighting members 25 to 29;

the switching on of the anti-D negative sighting member (16) lights up the − defining sighting member (29); and the switching on of the anti-D positive sighting member (20) lights up the + defining sighting member (28).

Since the O defining sighting member (27) is controlled by the lever 23 corresponding to the anti-AB serum, it follows that if lever 23 is actuated towards the negative sighting member 15 whilst the A, B or AB defining sighting members are already lit, the O defining sighting member (27) also lights up, thus indicating that an error of interpretation or handling has been made by the operator and this error is immediately brought to his attention since there is no such thing as an AO, BO or ABO blood group.

The wiring of the illustrated apparatus is designed in dependence on the order in which the mixtures of blood and test serum are deposited on the agglutination plate by the pipettes of the installation with which the apparatus is intended to cooperate. If the order of the mixtures is changed, the wiring is changed accordingly. The apparatus may also be separate and independent of the installation.

Figure 2:
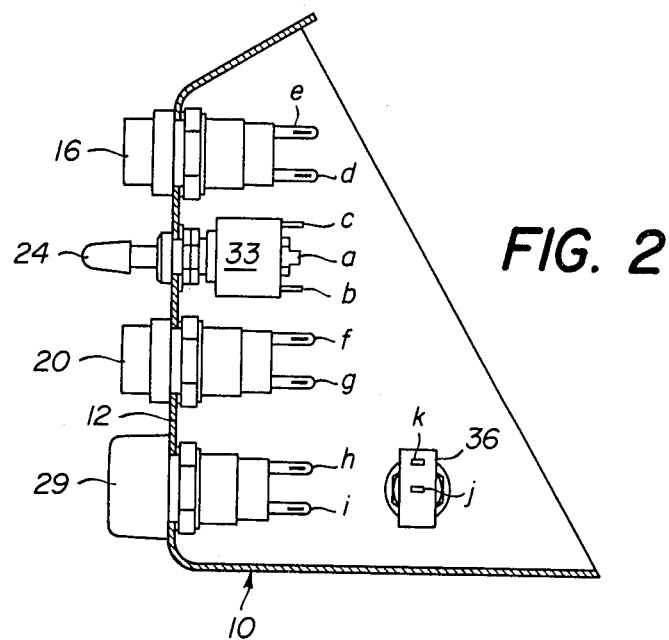
FIG. 2 is a sectional view of the apparatus shown in FIG. 1, along line II—II, turned counterclockwise through 30°.

Various modifications may be made to the apparatus described with reference to FIGS. 1 to 3. For instance, the sighting members 13 to 16 and the sighting members 17 to 20 could consist of non illuminable visual indicator elements, the face of these elements bearing a symbol for indicating a state of agglutination or of non-agglutination, or could even be replaced by only two visual indicator elements respectively bearing a common agglutinated state symbol and a common non-agglutinated state symbol.

Figure 4:
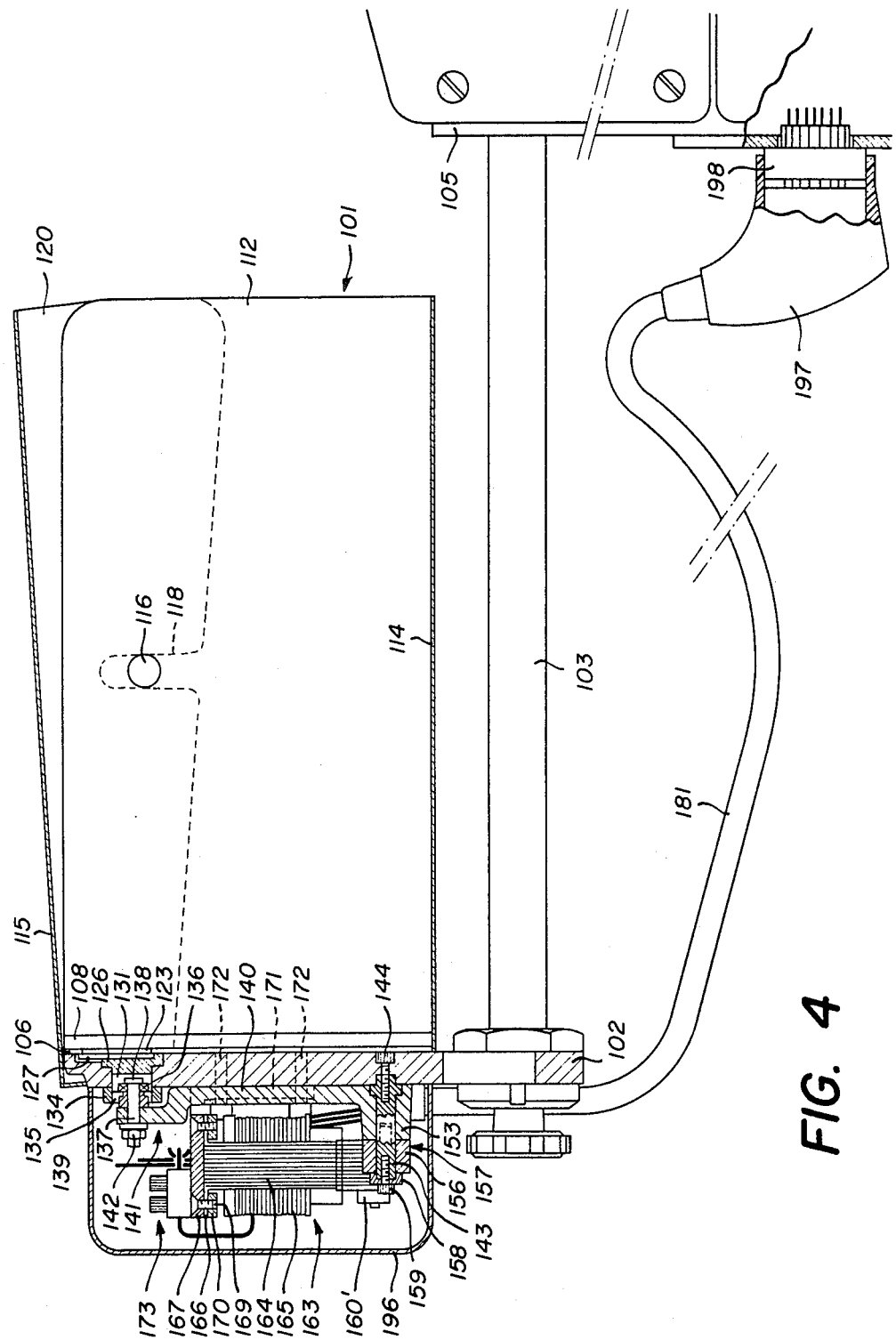
FIG. 4 is a sectional view, along line IV—IV of FIG. 5, of a projection box which is secured to the front of a blood typing installation of the kind set forth and whose bottom carries a display device forming part of another embodiment of the apparatus according to the invention.
Figure 5:
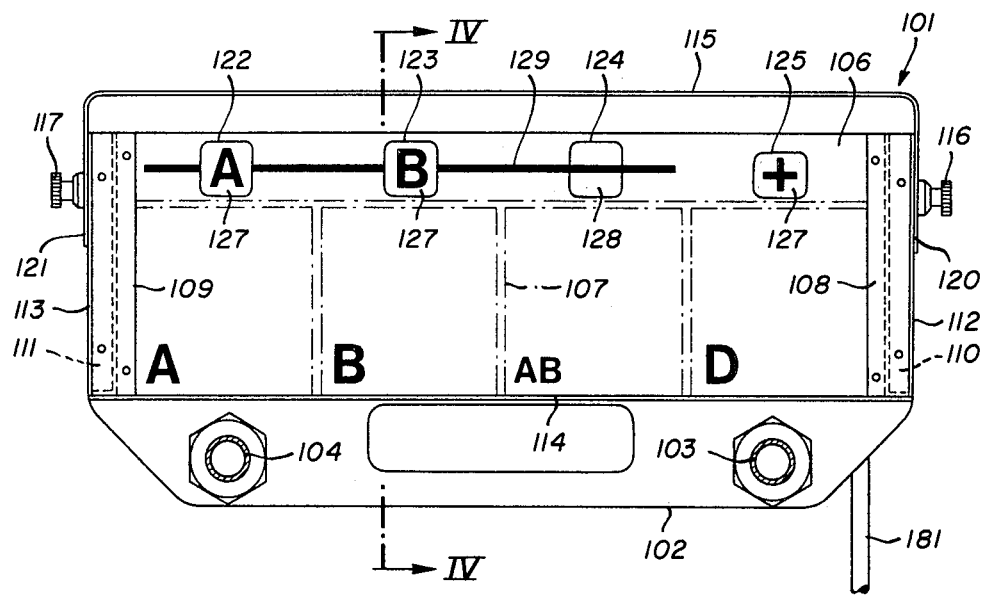
FIG. 5 is a front elevational view of the projection box of FIG. 4.
Figure 7:
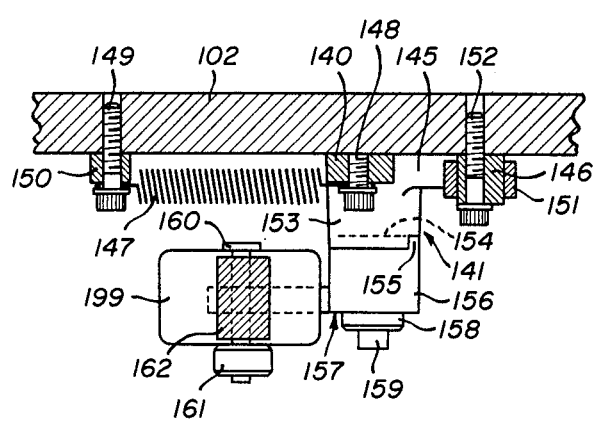
FIG. 7 is a section along line VII-VII of FIG. 6.

The projection box 101 shown in FIGS. 4 and 5 comprises an upright wall member 102 secured to the ends of two horizontal rods 103 and 104 able to slide in the front face of the framework 105 of a blood typing installation (not shown) provided with a camera and with an optical arrangement that enable the portrait of the individual whose blood is being typed and the abovementioned agglutination plate to be photographed at the same time, the image of the agglutination plate being projected by the optical arrangement with the aid of a suitable light source on to a screen 106, covering the inner surface of the wall member 102, that is directed towards the installation and the camera.

Such an installation is described and illustrated in French Pat. No. 75.00245. The projected image of the agglutination plate is shown in ghost lines at 107 in FIG. 5. In the lower left hand corners of the four squares defined by the image 107 are drawn or engraved on the screen 106 the letters A, B, AB and D. These letters serve to indicate the nature of the test-sera (listed above) used in the reactions obtained on the agglutination plate and of which the images are projected in the four squares. The screen 106 is held against the wall member 102 by clamps 108 and 109 which also serve to press against the wall member inwardly turned edge portions 110 and 111 provided on the side walls 112 and 113 of box 101. In addition to its base 114, the box 101 comprises a protective lid 115 that is angularly movable about the upper edge of the wall member 102 and that can be fixed in the required position by means of two clamping knobs 116 and 117 mounted on the side walls 112 and 113 and cooperating with two arcuate or elongated slots such as 118, in the side walls 120 and 121 of the lid.

Figure 8:
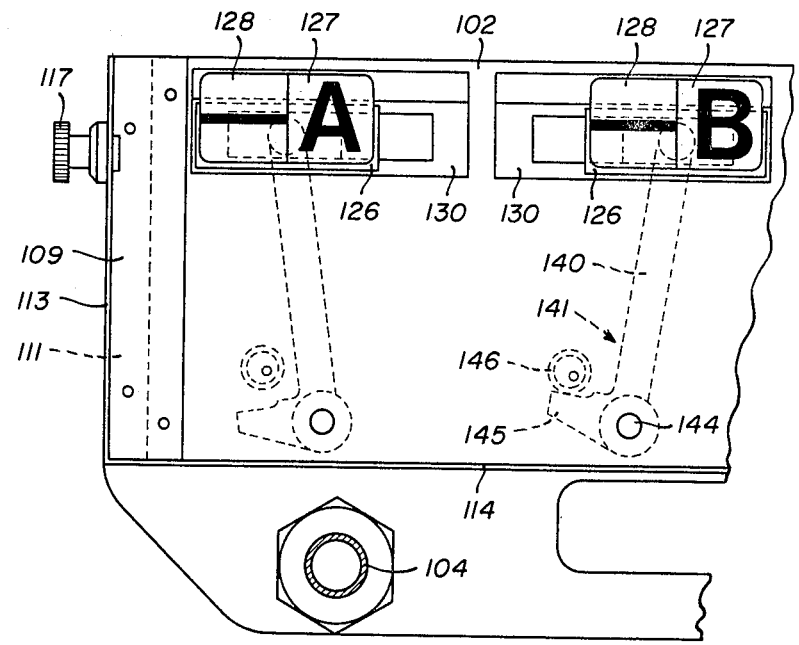
FIG. 8 shows a part of FIG. 5 after removal of its screen and of a protective lid.

In the screen 106, above the area reserved for the projected image 107, are four windows 122, 123, 124 and 125. Behind these windows are slidably mounted support elements 126 on each of which are secured a pair of plaquettes 127 and 128 each bearing information about the results obtainable on the agglutination plate. Thus, on the support element 126 sliding behind window 122 are secured a plaquette 127 bearing the letter A and a plaquette 128 crossed by a horizontal line (as may be seen in FIG. 8), on the support element 126 sliding behind the window 123 are secured a plaquette 127 bearing the letter B and a plaquette 128 crossed by a horizontal line (as may also be seen in FIG. 8), on the support element 126 sliding behind the window 124 are secured a plaquette 127 bearing the letter O and a plaquette 128 crossed by a horizontal line (as with the two preceding cases), and on the support element 126 sliding behind the window 125 are secured a plaquette 127 bearing a + (positive) sign and a plaquette 128 bearing a − (negative) sign. By actuating in an appropriate manner the sliding support elements 126, it is possible to display in the windows 122 to 125 any one of the conventional definitions A+, A−, B+, B−, AB+, AB−, O+ and O− of an individual's blood group, the horizontal line meaning "nothing" and only serving to establish the continuity of a line 129, draw or engraved on the screen 106, in the absence of a letter. This line 129, which stops short of the window 125, and the lines borne by the plaquettes 128 of the first three support elements only have an auxiliary function and can if desired be omitted.

The support elements 126 are mounted in stepped ports 130, of substantially rectangular cross-section, elongated in the horizontal direction, which extend through the wall member 102 opposite the windows 122 to 125. At the back, they are formed with two studs, such as 131, of substantially rectangular cross-section, which are spaced apart longitudinally of the support elements 126 and which extend through the ports 130 so as to have secured thereon, by means of screws 132 and 133 (FIG. 6), retaining elements 134 in such manner as to enable each support element 126 and associated retaining element 134 to move along its port 130 without however being able to move in a vertical or transverse direction. To this end in particular, the backs of the support elements 126 are further formed (FIG. 4) with longitudinally extending shoulders cooperating with one of the steps of the ports 130 and the retaining elements 134 overlap on to the longitudinal edges of the outer orifice of these ports 130.

The retaining elements 134 are each formed at their centre with a circular hole 135 through which may be inserted a ball bearing 136 for location between the studs 131 of the associated support element 126. Through the inner race of the bearing 136 extends a pin 137 having a head 138 bearing on the inside of this race. The outer race of each bearing 136 can move vertically to a certain extent between the studs 131, the vertical dimension of the latter being so selected as to enable such motion. The pin 137 then extends through a spacer 139 and the arm 140 of a bell-crank lever 141 to which it is secured by a nut 142.

The lever 141 is pivotally mounted on a pin 143 secured to the wall member 102 by a screw 144. It comprises a second arm 145 intended to abut against an eccentric stop 146 under the action of a tension spring 147 having one end attached to the arm by a screw 148 and having its other end attached to the wall member 102 by a screw 152. Because of its eccentricity its operative position can be adjusted.

Around its pivotal point, the lever 141 is formed with a boss 153 in the end face of which is provided a diametral groove 154. In this groove 154 is introduced a diametral tongue 155 provided on one of the end faces of a boss 156 formed at one end and around the pivotal point of a lever 157 also carried by the pin 143. The levers 141 and 157, which are thus rotationally interlocked, are held on the pin 143 by a screw 159.

The other end of the lever 157 is pivotally mounted on a pin 160 carried by a fork formed at the lower end of a plunger 162 of an electromagnet 163. The hole through which the pin 160 extends in the lever 157 is slightly elongated lengthwise of the latter to provide the pin 160 with play in this hole during the vertical to-and-fro movements of the plunger 162 in the body 164 of the electromagnet 163. A locking washer 161, having a grub screw, keeps the pin 160 in position.

The body 164 of the electromagnet 163, with its winding 165, is secured by flanges 166 to the underside of the limb 167 of a corner plate 168 by means of screws 169 and clamps 170, the other limb 171 of the corner plate 168 being secured to the wall member 102 by screws 172. The corner plate limb 171 is less wide than the limb 167 so as not to interfere with the angular movements of the lever arm 140. On the corner plate limb 167 is secured a connector 173 having two contact studs 174 and 175 to which are connected the ends $165^1$ and $165^2$ of the winding 165.

Figure 6:
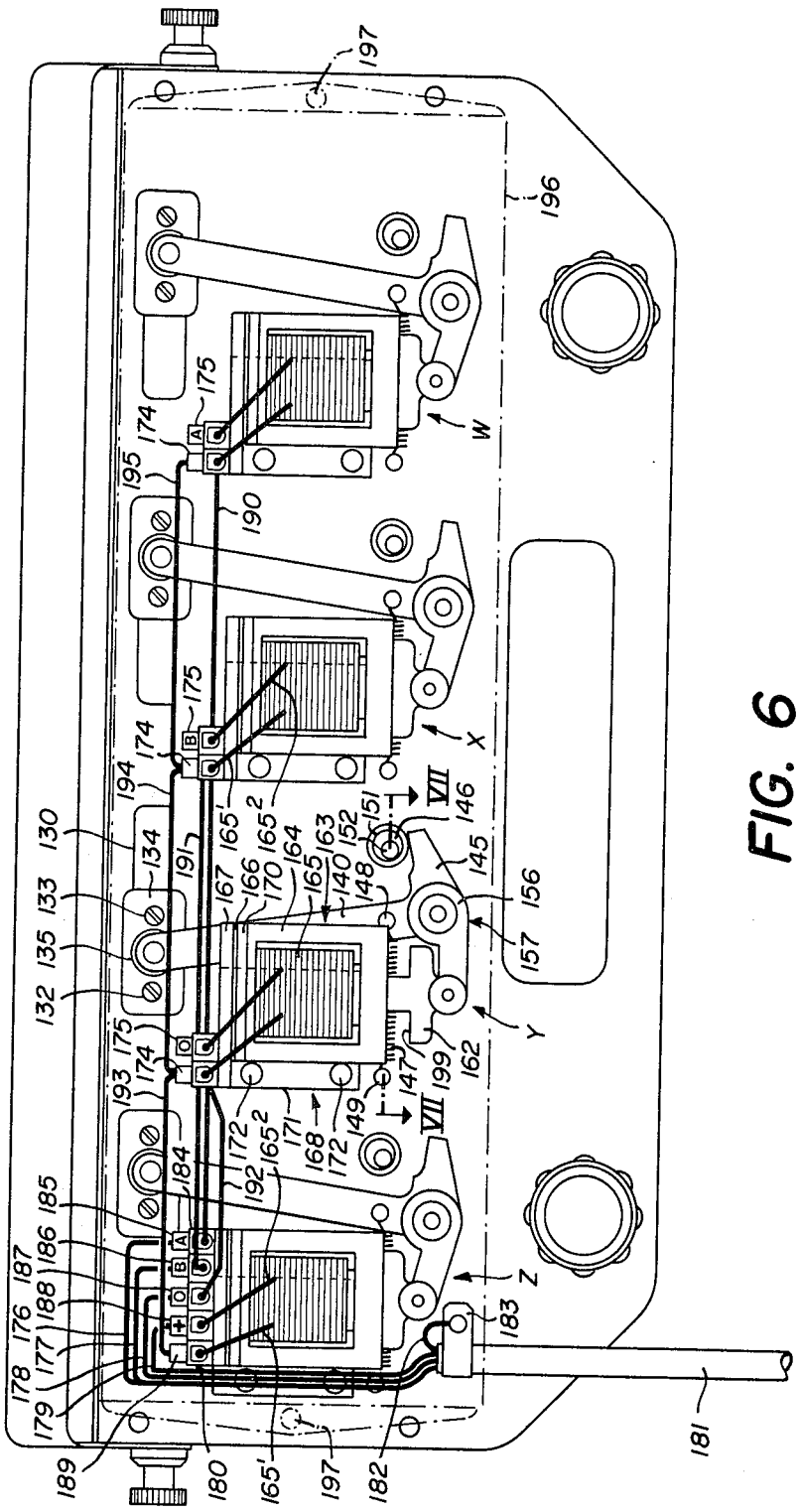
FIG. 6 is a rear view of the projection box showing the display device from the rear after removal of its shielding cover.

As will be observed from FIG. 6, the display device comprises four separate mechanisms W, X, Y and Z respectively cooperating with the windows 122 to 125. The mechanisms W, X and Y are identical. The mechanism Z differs slightly from the other three, firstly, because the limb 167 of its corner plate 168 is less wide than in the other cases to facilitate the fitting of five electrical conductors 176, 177, 178, 179 and 180 of a six-conductor supply cable 181, the sixth conductor, 182, being earthed by a cramp 183 securing the cable 181 to the wall member 102, and, secondly, because the limb 167 carries a connector 184 having five contact studs 185, 186, 187, 188 and 189 to which the conductors 176 to 180 are respectively connected.

The stud 185 is connected to the stud 175 (W) by a conductor 190, the stud 186 is connected to the stud 175 (X) by a conductor 191, the stud 187 is connected to the stud 175 (Y) by a conductor 192, the stud 188 is connected to the end 165² of the winding 165 (Z) and the stud 189 is connected, firstly, to the end 165¹ of the winding 165 (Z) and, secondly, to the studs 174 (Y), 174 (X) and 174 (W) by conductors 193, 194 and 195.

The display device is shielded by a cover 196 secured to the wall member 102 by screws 197 (the cover 196 and the screws 197 are shown in ghost lines in FIG. 6).

Figure 9:
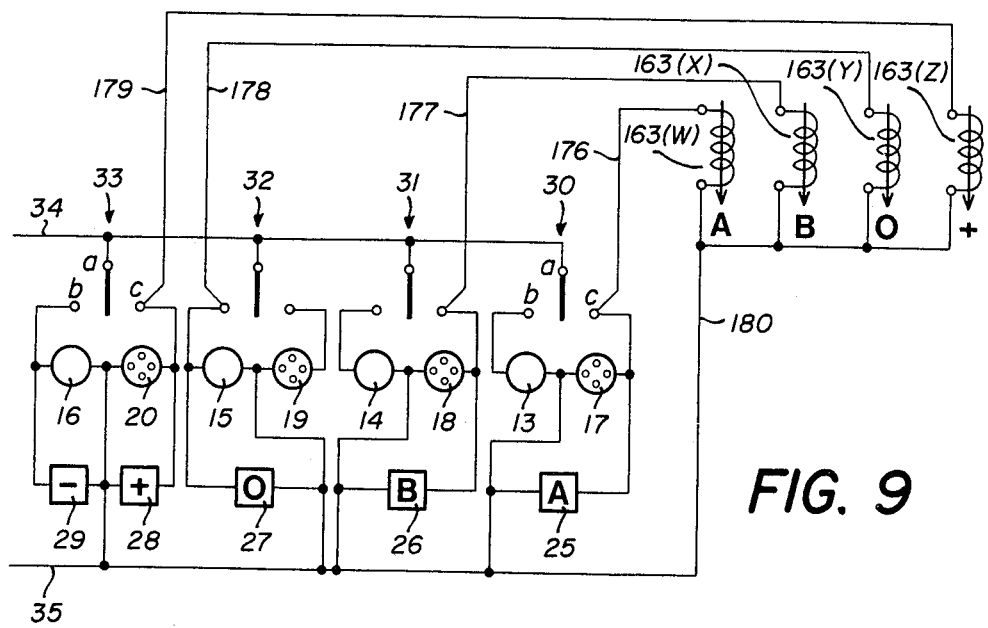
FIG. 9 is an electrical diagram.

The cable 181 is terminated by a multi-pin plug 197 pressed into a corresponding electric current socket 198 secured to the framework 105 of the installation and electrically connected to the circuit of FIG. 3 in accordance with the diagram of FIG. 9. As is apparent from this diagram, the conductors 176, 177 and 179 are connected to the terminals c of the switches 30, 31 and 33 respectively, the conductor 178 is connected to the terminal b of the switch 32, and the conductor 180 is connected to the conductor 35.

The operation is as follows: the operator actuates the levers of switches 30 to 33 in dependence on the results of the reaction that have occurred on the agglutination plate. When a reaction has been positive, i.e. when agglutination has taken place, he actuates the corresponding switch to connect its terminal a, which is connected to the supply conductor 34, to its terminal c and when a reaction has been negative, i.e. when no agglutination has taken place, he actuates the corresponding switch to connect its terminal a to its terminal b. With the switches 30, 31 and 33, actuation thereof to connect their terminals a to the terminals c lights up the luminous, positive result, sighting members 17, 18 and 20 and the luminous, definition, sighting members 25 (A), 26 (B) and 28 (+), respectively, and moreover energizes the electromagnets 163 (W), 163 (X) and 163 (Z), respectively; actuation thereof to connect their terminal a to their terminal b only lights up the luminous, negative result, sighting members 13 and 14 in the case of the switches 30 and 31, and lights up both the luminous, negative result, sighting member 16 and the luminous, definition, sighting member 29 (−) in the case of the switch 33. With the switch 32, actuation thereof to connect its terminal a to its terminal c only lights up the luminous, positive result, sighting member 19, and actuation thereof to connect its terminal a to its terminal b lights up both the luminous, negative result, sighting member 15 and the luminous, definition, sighting member 27 (O).

The energization of an electromagnet 163 causes its plunger 162 to rise and consequently the interlocked levers 157 and 141 to rock from their inoperative position (that occupied by the levers in mechanisms W, X and Z) where shoulders 199 come into abutment with the body or yoke 164 of the electromagnet.

In the operative position of their levers 141 and 157, the mechanisms W, X and Y cause the letters A, B and O to appear in the windows 122, 123 and 124, respectively.

In the inoperative position of the levers 141 and 157, in which they are rocked by the return spring 147 after deenergization of the electromagnet 163, the mechanisms W, X and Y cause the horizontal line borne by the plaquettes 128 to appear in these same windows.

In the case of the mechanism Z, the latter causes the sign + to appear in the operative position of its levers 141 and 157 and the sign − to appear in the inoperative position of the latter.

The possibility of being able to display the various conventional definitions listed earlier, directly on to the screen at the location that was normally occupied by the projected image of an auxiliary plate, makes it possible to eliminate the operation which consists in selecting this auxiliary plate, with the inherent possibility of an error that exists, and in placing it next to the agglutination plate in the installation.

The definition displayed in the windows and the projected image 107 of the agglutination plate are photographed together, as also the portrait of the individual whose blood has been typed and who is placed behind the projection box 101 (to the left thereof in FIG. 4), by means of the camera provided in the installation.

This second embodiment described and illustrated with reference to FIGS. 4 to 9, by way of example, can be modified in a variety of ways. For instance, the support elements 126 could move vertically under the direct action of the plungers 162 of the electromagnets 163.

Further, the luminous, definition, sighting members 25 to 29 could be dispensed with although it is preferably to keep them to enable the operator to be warned of any interpretation or handling error he may have committed, as would in particular be the case should an AO, BO or ABO group be displayed by these luminous sighting members.

We claim:

1. Apparatus for displaying in indication form, A, B, AB or O followed by the sign + or −, the results which enable an individual's blood group to be typed and which are obtained on an agglutination support with mixtures of blood taken from the individual and of different, appropriate, test sera, said apparatus comprising at least one positive visual indicator element, representing a state of agglutination of said mixtures, at least one negative visual indicator element, representing a state of non-agglutination of said mixtures, which is spaced from said first element, a plurality of electrical switches corresponding in number to that of said mixtures and controlled by levers which are disposed between said visual indicator elements and which are each manually actuable towards one or other of said elements, from a middle position, depending on the results obtained with said mixtures, and sighting members causing the letters A, B and O and the signs + and − to appear in dependence on the direction in which the levers are actuated to display the definition of said blood group.

2. Apparatus according to claim 1, comprising a plurality of positive indicator elements and a plurality of negative indicator elements corresponding in number to that of the levers, the positive indicator elements being so disposed in relation to the negative indicator elements as to form pairs and the levers being each disposed between one of said pairs.

3. Apparatus according to claim 2, wherein the indicator elements comprise luminous sighting members electrically connected to the switches, each of said sighting members being arranged only to light up when the associated lever is actuated towards it.

4. Apparatus according to claim 1, wherein the sighting members comprise luminous sighting members electrically connected to the switches and respectively bearing the letters A, B and O and the signs + and −, said members lighting up in dependence on the direction in which the levers are actuated.

5. Apparatus according to claim 1, for use with an installation for typing an individual's blood comprising a screen on to which are projected the results obtained on an agglutination support, wherein the sighting members comprise windows formed in said screen, the letters A, B and O and the signs + and − being borne by movable support elements behind the windows.

6. Apparatus according to claim 5, wherein the movable support elements are actuated by electromagnets controlled by the switches.

7. In a blood-typing installation comprising means for supporting at a position where it can be visually examined an agglutination support carrying, at given discrete locations, a series of blood tests each with a mixture of blood taken from an individual and an appropriate test serum, said blood tests having visually perceptible results depending on a state of agglutination and a state of non-agglutination of said mixtures, a display apparatus for providing indications, A, B, AB or O followed by + or −, of the results of said tests, said apparatus comprising a control panel located adjacent said supporting means;

a plurality of manually-actuatable switch members disposed on the control panel at locations corresponding to respective ones of said given locations on an agglutination support carried by the supporting means;

positive and negative indication means associated with the switch members for providing, when the switch members are actuated according to the results of the tests after visual examination of an agglutination support carried by the supporting means, positive and negative indications representing respectively said state of agglutination and said state of non-agglutination of said mixtures corresponding to the results of the tests, said positive and negative indications being disposed spaced apart from one another on the control panel and in correlation with the locations of the switch members; and display means for selectively displaying the letters A, B, O and the signs + and − in response to actuation of said switch members and in correspondence with said positive and negative indications corresponding to the results of the tests.

8. In a blood-typing installaton comprising means for supporting at a position where it can be visually examined an agglutination support carrying at given discrete locations, a series of blood tests each with a mixture of blood taken from an individual and an appropriate test serum, said blood tests having visually perceptible results depending on a state of agglutination and a state of non-agglutination of said mixtures, and a screen for receiving a projected image of the results of said series of tests on an agglutination support carried by said supporting means, said screen forming part of a recording arrangement for (a) a picture of an individual whose blood is being typed, (b) a reproduction of the results of said series of blood tests, and (c) an indication A, B, AB or O followed by + or − corresponding to the results of said series of blood tests, an apparatus for providing said indication adjacent said screen, said apparatus comprising a control panel located adjacent said supporting means;

a plurality of manually-actuatable switch members disposed on the control panel at locations corresponding to respective ones of said given locations on an agglutination support carried by the supporting means;

positive and negative indication means associated with the switch members for providing, when the switch members are actuated according to the results of the tests after visual examination of an agglutination support carried by the supporting means, positive and negative indications representing respectively said state of agglutination and said state of non-agglutination of said mixtures corresponding to the results of the tests, said positive and negative indications being disposed spaced apart from one another on the control panel and in correlation with the locations of the switch members; and display means adjacent said screen for selectively displaying the letters A, B, O and the signs + and − in response to actuation of said switch members and in correspondence with said positive and negative indications corresponding to the results of the tests.

9. Apparatus according to claim 8, comprising second display means on said control panel for providing a visible display.

* * * * *